US009262819B1

(12) United States Patent
Kagalwala et al.

(10) Patent No.: US 9,262,819 B1
(45) Date of Patent: Feb. 16, 2016

(54) SYSTEM AND METHOD FOR ESTIMATING SPATIAL CHARACTERISTICS OF INTEGRATED CIRCUITS

(71) Applicant: GLOBALFOUNDRIES INC., Grand Cayman (KY)

(72) Inventors: Taher E. Kagalwala, Wappingers Falls, NY (US); Narender Rana, Highland, NY (US); Yunlin Zhang, Wappingers Falls, NY (US)

(73) Assignee: GlobalFoundries, Inc., Grand Cayman (KY)

( * ) Notice: Subject to any disclaimer, the term of this patent is extended or adjusted under 35 U.S.C. 154(b) by 0 days.

(21) Appl. No.: 14/497,969

(22) Filed: Sep. 26, 2014

(51) Int. Cl.
*G06K 9/00* (2006.01)
*G06T 7/00* (2006.01)
*H01J 37/28* (2006.01)
*G01N 23/225* (2006.01)
*G01Q 60/24* (2010.01)

(52) U.S. Cl.
CPC ............ *G06T 7/0002* (2013.01); *G01N 23/225* (2013.01); *G01Q 60/24* (2013.01); *H01J 37/28* (2013.01); *G06T 2207/30148* (2013.01)

(58) Field of Classification Search
USPC ............ 382/141, 145, 147, 149, 152; 348/86, 348/126
See application file for complete search history.

(56) References Cited

U.S. PATENT DOCUMENTS

| 5,861,320 A * | 1/1999 | Shiraishi | G03F 9/70 257/E23.179 |
| 6,667,806 B2 * | 12/2003 | Yoshitake | G03F 7/70633 257/E21.525 |
| 6,703,170 B1 * | 3/2004 | Pindo | G03F 1/144 430/30 |

(Continued)

FOREIGN PATENT DOCUMENTS

| WO | 2005003911 A2 | 1/2005 |
| WO | 2007124294 A2 | 11/2007 |
| WO | 2012150993 A2 | 11/2012 |

OTHER PUBLICATIONS

Xiao, Q.L. et al.; "Estimating the height and width of integrated circuit building block from the schematics"; Proceedings of the Sixth Australian Conference on Neural Networks (ACNN'95), pp. 181-184; 1995.

(Continued)

*Primary Examiner* — Yosef Kassa
(74) *Attorney, Agent, or Firm* — Anthony J. Canale; Hoffman Warnick, LLC

(57) ABSTRACT

Methods of the present disclosure can include a method for estimating a spatial characteristic of an integrated circuit (IC), the method comprising: calculating a correlation between a dimension of a photoresist layer and exposure to a scanning electron microscope (SEM) for at least one reference IC pattern in the photoresist layer, the correlation providing a relationship between the dimension of the photoresist and the spatial characteristic, wherein the calculating is based on: an SEM image of the at least one reference IC pattern produced from reducing the dimension of the photoresist layer with the SEM from an initial value to a reduced value, the initial value of the dimension, and the reduced value of the dimension; and estimating the spatial characteristic of a target IC based on the correlation.

20 Claims, 6 Drawing Sheets

(56) References Cited

U.S. PATENT DOCUMENTS

| | | | |
|---|---|---|---|
| 6,965,895 B2 | 11/2005 | Smith et al. | |
| 7,114,138 B1 | 9/2006 | Teig et al. | |
| 7,186,488 B2 * | 3/2007 | Nagai | G03F 7/70625 430/30 |
| 7,523,076 B2 | 4/2009 | Drege et al. | |
| 7,539,585 B2 | 5/2009 | Baseman et al. | |
| 7,655,369 B2 * | 2/2010 | Asano | G03F 1/144 430/22 |
| 8,126,677 B2 * | 2/2012 | De Groot | G01B 11/06 356/512 |
| 8,466,569 B2 * | 6/2013 | Meisner | G03F 9/7076 257/764 |
| 2002/0090744 A1 | 7/2002 | Brill et al. | |
| 2008/0275586 A1 | 11/2008 | Ko et al. | |
| 2012/0078827 A1 | 3/2012 | Nugent | |
| 2012/0150993 A1 | 6/2012 | Flack et al. | |

OTHER PUBLICATIONS

Xiao, Q.L. et al.; "Neural network based estimation of VLSI building block dimensions from schematics"; 1995 IEEE Symposium on Circuits and Systems; pp. 381-384; vol. 1, IEEE; 1995.

IBM; "Self learning method to predict a workload indicator for provisioning of resources"; An IP.com Prior Art Database Technical Disclosure; http://ip.com/IPCOM/000158172D; Sep. 18, 2007.

Spi Dst et al.; "Neural Networks, Pattern Recognition, and Fingerprint Hallucination"; An IP.com Prior Art Database Technical Disclosure; http://ip.com/IPCOM/000147933D; Mar. 28, 2007.

* cited by examiner

SYSTEM AND METHOD FOR ESTIMATING SPATIAL CHARACTERISTICS OF INTEGRATED CIRCUITS

BACKGROUND

The present invention relates generally to estimating the spatial characteristics of integrated circuits. Spatial characteristics can include a length, width, height, critical dimension, side wall angle and/or profile, line edge, line width, roughness, shape contour, undercut, foot, a complete profile in one or more dimensions, or other measurement of a feature. More specifically, the present disclosure provides methods, program products, and systems for estimating a spatial characteristic of an integrated circuit, which can use one or more artificial neural networks.

An integrated circuit ("IC") is a device (e.g., a semiconductor device) or electronic system that includes many electronic components, such as transistors, resistors, diodes, etc. These components can be interconnected to form multiple circuit components, such as gates, cells, memory units, arithmetic units, controllers, decoders, etc. An IC includes multiple layers of wiring that interconnect its electronic and circuit components.

Fabrication foundries ("fabs") can manufacture ICs using photolithographic processes. Photolithography is an optical printing and fabrication process by which patterns on a photolithographic mask (i.e., photomask) are imaged and defined onto a photosensitive layer coating of a substrate. To fabricate an IC, photomasks are created using an IC design layout as a template. The photomasks contain the various geometries (i.e., features) of the IC design layout, and these geometries can be separated with layers of photoresist material. The various geometries contained on the photomasks correspond to the various base physical IC elements that make up functional circuit components such as transistors, interconnect wiring, via pads, as well as other elements that are not functional circuit elements but are used to facilitate, enhance, or track various manufacturing processes. Through sequential use of the various photomasks corresponding to a given IC in an IC fabrication process, a large number of material layers of various shapes and thicknesses with various conductive and insulating properties may be built up to form the overall IC and the circuits within the IC design layout.

A pitch specifies a sum of the width of a feature and the space on one side of the feature separating that feature from a neighboring feature. The pitch for a particular IC structure is generally predetermined and fixed by design. Depending on the photolithographic process being used, factors such as optics and wavelengths of light or radiation restrict how small the distance between two features (also known as "critical dimension") can be before features can no longer be reliably printed to a wafer or mask. Thus, the pitch limits the largest size of any features that can be created on a wafer.

Several constraining factors in traditional photolithographic processes limit their effectiveness as circuit complexity continues to increase and transistor designs become more advanced and ever smaller in size (i.e., density shrink). Some such constraining factors are the lights/optics used within the photolithographic processing systems. Specifically, the light/optical tools or techniques available for use may be limited due to physical constraints (e.g., wavelength and aperture) of the photolithographic process. Further, physical probes (e.g., atomic force microscopy (AFM) probes) for measuring the spatial characteristics may have limited effectiveness for IC elements smaller than some dimensions of the probe. Other measuring techniques, such as the use of a scanning electron microscope (SEM), may emit electrons which reduce one or more dimensions of the IC being measured (e.g., by degrading the material composition of a particular layer). Despite the limitations of these techniques, measuring the spatial characteristics of an IC with high accuracy can ensure the quality and reliability of each feature in an IC product produced from a manufacturing line.

SUMMARY

A first aspect of the present disclosure provides a method for estimating a spatial characteristic of an integrated circuit (IC), the method comprising: calculating a correlation between a dimension of a photoresist layer and exposure to a scanning electron microscope (SEM) for at least one reference IC pattern in the photoresist layer, the correlation providing a relationship between the dimension of the photoresist and the spatial characteristic, wherein the calculating is based on: measurements derived from an SEM image of the at least one reference IC pattern produced from reducing the dimension of the photoresist layer with the SEM from an initial value to a reduced value, the initial value of the dimension, and the reduced value of the dimension; and estimating the spatial characteristic of a target IC based on the correlation.

A second aspect of the present disclosure provides a program product stored on a computer readable storage medium, the program product operative to a spatial characteristic of an integrated circuit (IC) when executed, the computer readable storage medium comprising program code for: calculating, using an artificial neural network (ANN), a correlation between a dimension of a photoresist layer and exposure to a scanning electron microscope (SEM) for at least one reference IC pattern including the photoresist layer, the correlation providing a relationship between the dimension of the photoresist and the spatial characteristic, wherein the calculating is based on: measurements derived from an SEM image of the at least one reference IC pattern produced from reducing the dimension of the photoresist layer with the SEM from an initial value to a reduced value, the initial value of the dimension, and the reduced value of the dimension; and estimating the spatial characteristic of a target IC based on the correlation.

A third aspect of the present disclosure provides a system for estimating a spatial characteristic of an Integrated Circuit (IC), the system comprising: a computing device in communication with a scanning electron microscope (SEM) and an atomic force microscopy (AFM) probe, and including program code for: calculating a correlation between a dimension of a photoresist layer and exposure to the scanning electron microscope (SEM) for at least one reference IC pattern including the photoresist layer, the correlation providing a relationship between the dimension of the photoresist and the spatial characteristic, wherein the calculating is based on: measurements derived from an SEM image of the at least one reference IC pattern produced from reducing the dimension of the photoresist layer with the SEM from an initial value to a reduced value, the initial value of the dimension, and the reduced value of the dimension, wherein one of the initial value and the reduced value of the dimension are obtained with the AFM probe; and estimating the spatial characteristic of a target IC based on the correlation.

BRIEF DESCRIPTION OF THE SEVERAL VIEWS OF THE DRAWINGS

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION

Figure 1:
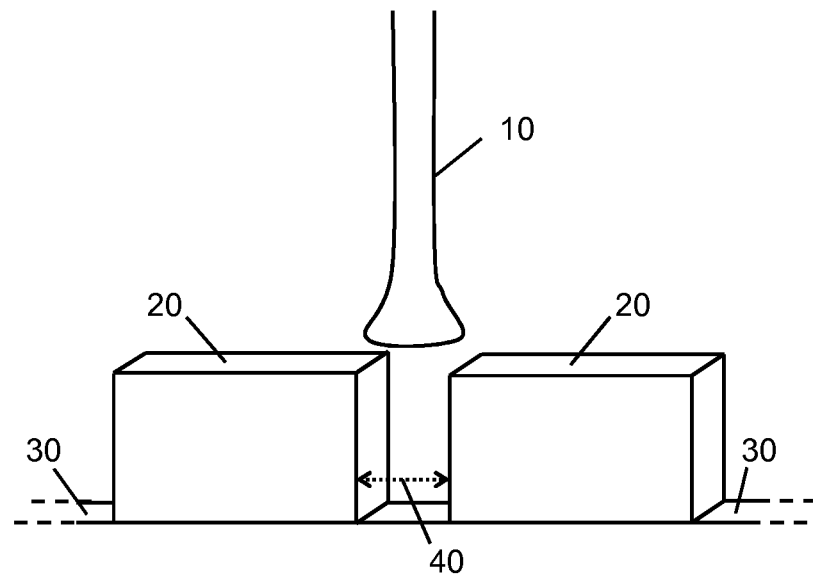
FIG. 1 is a perspective view of an atomic force microscopy (AFM) probe and integrated circuit (IC) elements according to an embodiment of the present disclosure.

In the following description, reference is made to the accompanying drawings that form a part thereof, and in which is shown by way of illustration specific exemplary embodiments in which the present teachings may be practiced. These embodiments are described in sufficient detail to enable those skilled in the art to practice the present teachings, and it is to be understood that other embodiments may be used and that changes may be made without departing from the scope of the present teachings. The following description is, therefore, merely illustrative.

In the semiconductor industry, "metrology" refers to the study of measurements and tools for measuring integrated circuit (IC) materials, in addition to techniques for improving the accuracy of these tools. Aspects of the present disclosure relate to metrology techniques, and more specifically include using a combination of measurements to estimate with accuracy the spatial characteristics of a target IC pattern, including situations where a feature cannot be measured using physical probes or other instruments for obtaining direct measurements. As used herein, the term "spatial characteristic" can include without limitation: a length, a width, a critical dimension, a height, a side wall angle and/or profile, a line edge, a line width, a roughness, a shape contour, an undercut, a footprint, a complete profile in one or more dimensions, and/or any other measurement of a particular circuit feature. Furthermore, the term "estimate" or "estimating" refers to the process of calculating a particular value or measurement of an item, object, feature, etc. based on other quantities, without performing a direct measurement of the object, item, feature, etc. being estimated. In some contexts, the term "estimate" or "estimating" can refer to predicting (i.e., estimating a future value or measurement) the quantity for a particular object, item, feature, etc.

The present disclosure can be embodied as a method for estimating a spatial characteristic of an IC. The method can include, at one step, calculating a correlation between at least one dimension (e.g., a length, width, height, etc.) of a photoresist layer and exposure to a scanning electron microscope (SEM). More specifically, the IC can be subject to a top-down exposure from the SEM. As used herein, the term "correlation" can include one or more of several mathematical quantities and/or models, and as examples can include, e.g., a data set and/or function which relates a particular dimension of an IC pattern with exposure (e.g., top-down exposure) to an SEM. Furthermore, the correlation can be any type of mathematical relationship between two or more variables, and is not exclusive to linear correlations. In further addition, the correlation can provide a relationship between a dimension of an IC pattern and a desired spatial characteristic, e.g., though intervening factors and variables, such as design constraints or predetermined patterns. Exposure to the SEM can be measured in terms of, e.g., time, number of electrons which contact the IC pattern or a particular layer, and/or other types of variables. The correlation can be calculated with respect to at least one reference IC pattern which includes the photoresist layer to be modeled. In a particular embodiment, this correlation can be calculated by training an artificial neural network (ANN) to computationally model the correlation, e.g., by adjusting several weighted factors for an estimated function and updating the estimate several times using test data and/or reference data.

Many types of data can be used to calculate the correlation. For example, the method can use an SEM image (e.g., produced from a top-down scan) produced from reducing the dimension of the photoresist layer of the reference IC pattern, with the SEM, from an initial value to a reduced value. More specifically, embodiments of the method can use the SEM image itself and/or measurements derived from the SEM image. The method can also include using the initial physical value of the dimension (e.g., measured using an atomic force microscopy (AFM) probe), the reduced value of the dimension (e.g., measured with the SEM), and the final physical value of the dimension (e.g., measured using an AFM probe) to calculate attributes of the correlation. In the case of a small IC pattern not physically measurable using a physical probe (e.g., an AFM probe), a reduction in line width and widening of adjacent space after the SEM measurement can allow a user to physically measure the reduced value of the dimension. Thus, embodiments of the present disclosure can be used for small pattern metrology. After a value of the correlation is calculated, the method can include estimating one or more spatial characteristics of a target IC pattern using the correlation, e.g., by combining the correlation with known features of a target IC pattern, optionally with other inputs.

FIG. 1 illustrates an atomic force microscopy (AFM) probe 10 for measuring an IC pattern at the location of a photoresist layer 20. As used herein, a photoresist material can refer to a photo-sensitive material used in photolithography to transfer a pattern from a mask onto a wafer. For example, photoresist layer 20 can include a liquid deposited on the surface of the wafer as a thin film solidified with a low temperature anneal. Photoresist layer 20 can be positioned or patterned (e.g., by removal of a deposited photoresist) in contact with a substrate 30 and may include gaps therein. In the areas where photoresist layer 20 can be reached by UV radiation, photochemical reactions change its properties, e.g., solubility. Each photoresist structure can have a substantially similar height and thus can make up a single photoresist layer 20. Photoresist layer 20 can be placed upon substrate 30 to define regions where portions of substrate 30 can be removed, processed, etc. in various manufacturing process steps. To manufacture IC products with consistent function and quality, IC design patterns can include a particular size for the space between and within photoresist layers 20. The separation distance between one region of photoresist and another can be known as a critical dimension 40.

AFM probe 10, in some cases, may have a greater diameter than critical dimension 40. In this case, as is shown in FIG. 1, AFM probe 10 may not accurately measure critical dimension 40 and/or the spatial characteristics of photoresist layers 20. Some IC patterns may include a critical dimension 40 of less than approximately, e.g., forty nanometers (nm). AFM probe 10 may be unable to contact sidewalls of at least one photoresist layer 20 for critical dimensions 40 of this size because of constraints such as tip shape, size, etc. Thus, AFM probe 10 may have a limited ability to measure some critical or small IC patterns.

Figure 2:
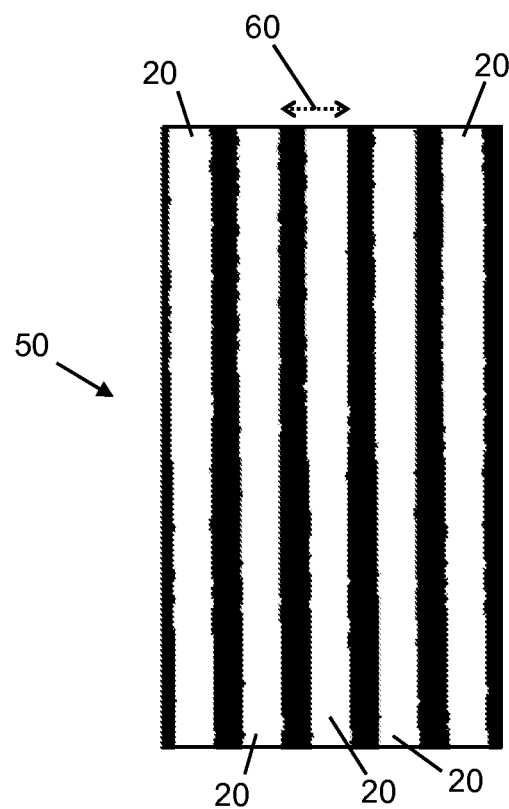
FIG. 2 is an example of a scanning electron microscope (SEM) image of an IC pattern according to an embodiment of the present disclosure.

Turning to FIG. 2, an example SEM image of an IC pattern 50 is shown. The example SEM image shown in FIG. 2 is a top-down exposure of IC pattern 50 to the SEM. One or more SEM scans can measure an IC pattern 50 where AFM probe 10 (FIG. 1) is ineffective, as a beam of electrons emitted from the SEM is not limited by the probe shape and size requirements of AFM probe 10 (FIG. 1) discussed herein. Contact between the emitted electrons and IC pattern 50 can cause some of the structure of photoresist layer 20 to degrade, thereby reducing one or more dimensions of the material (e.g., reducing a length, height, width, etc.). Although an SEM scan can accurately measure space between adjacent photoresist materials of photoresist layer 20, electrons emitted from the SEM can degrade the structures which make up a particular design. In some cases, even a single SEM scan can render photoresist layer 20 inoperable for its intended purpose. However, pitch 60 from one photoresist layer 20 to an adjacent photoresist layer 20 may remain constant after each SEM scan is applied, because degraded portions of photoresist layer 20 become empty space above substrate 30.

Embodiments of the present disclosure can estimate dimensions of an IC with features which cannot be measured with a physical probe, or which cannot be exposed to an SEM scan without unacceptably reducing the feature's size. In some embodiments, these estimations can be performed using an artificial neural network (ANN). For clarity, the operation of an ANN in embodiments of the present disclosure is discussed.

Figure 3:
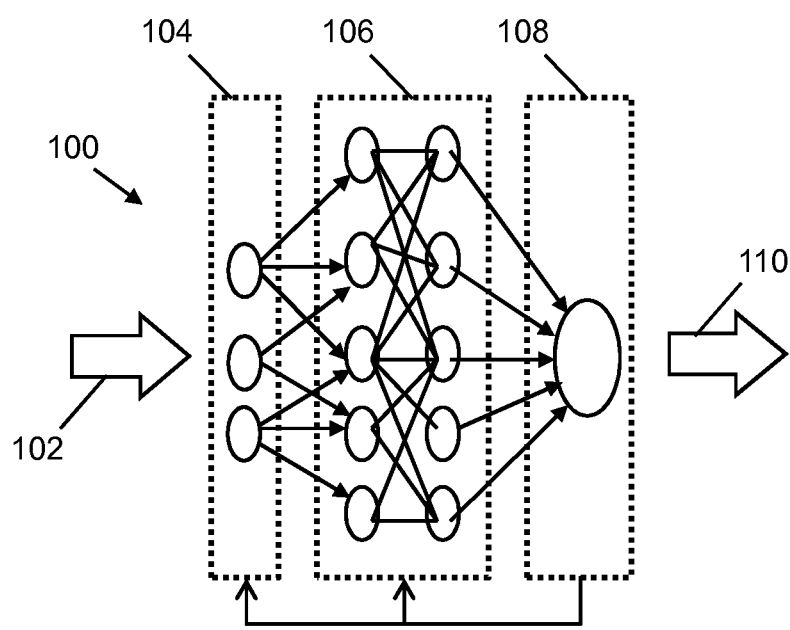
FIG. 3 is an example diagram of an artificial neural network (ANN) according to an embodiment of the present disclosure.

Turning to FIG. 3, an example ANN 100 is shown. ANN 100 may represent at least part of one or more computer systems and/or software components which can be programmed, adapted, or otherwise used to carry out process steps in embodiments of the present disclosure. Embodiments of the present disclosure can be carried out with multiple ANNs 100, and illustrative embodiments which use multiple ANNs 100 are discussed elsewhere herein. The architecture of an example computer system, which may include one or more ANNs 100, is also discussed herein by reference to FIG. 4.

ANN 100 can create (e.g., by machine learning) a model which relates one or more input variables to a particular output variable. As successive groups of inputs are provided to ANN 100, the created model can be adjusted based on comparing various outputs to verified, ideal values and/or other related groups of inputs and outputs. Thus, inputs 102 denote a group of inputs provided to ANN 100. An input layer 104 represented by one or more nodes. Each node of input layer 104 can in turn be connected to other nodes in a hidden layer 106, which represent particular mathematical functions. In embodiments of the present disclosure, inputs 102 to input layer 104 can include, e.g., measurements from an SEM image or one or more physical probes, such as AFM probe 10. Each node of hidden layer 106 can include a corresponding weight ("W") representing a factor or other mathematical adjustment for converting input variables into output variables. The nodes of hidden layer 106 can eventually connect to the node of an output layer 108, which provides an output 110 corresponding to inputs 102.

To increase the accuracy of ANN 100, output values of output layer 108 can be compared with predetermined or ideal values to calculate errors in a process known as "error backpropagation." Where the error between an output of output layer 108 and a predetermined value exceeds a particular threshold, ANN 100 can include processes for self-correction. For example, process steps encoded in hardware and/or software can use values in output layer 108 to adjust weights W of hidden layer 106 and/or connections between nodes of input layer 104 and hidden layer 106. In an example embodiment, error backpropgagation can include "Bayesian Regulation," a series of mathematical steps leveraging probability for weight calculations in order to minimize the mean squared error (MSE) (i.e., the squared value of the difference between an output and a predetermined value, whether positive or negative) between values in output layer 108 and the predetermined values. Bayesian Regulation can help generalize the model and avoids over fitting experimental data to a particular model. Thus, ANN 100 can develop and adjust models by processing multiple inputs 102 to calculate outputs 108 and compare outputs 108 to predetermined or expected values.

Figure 4:
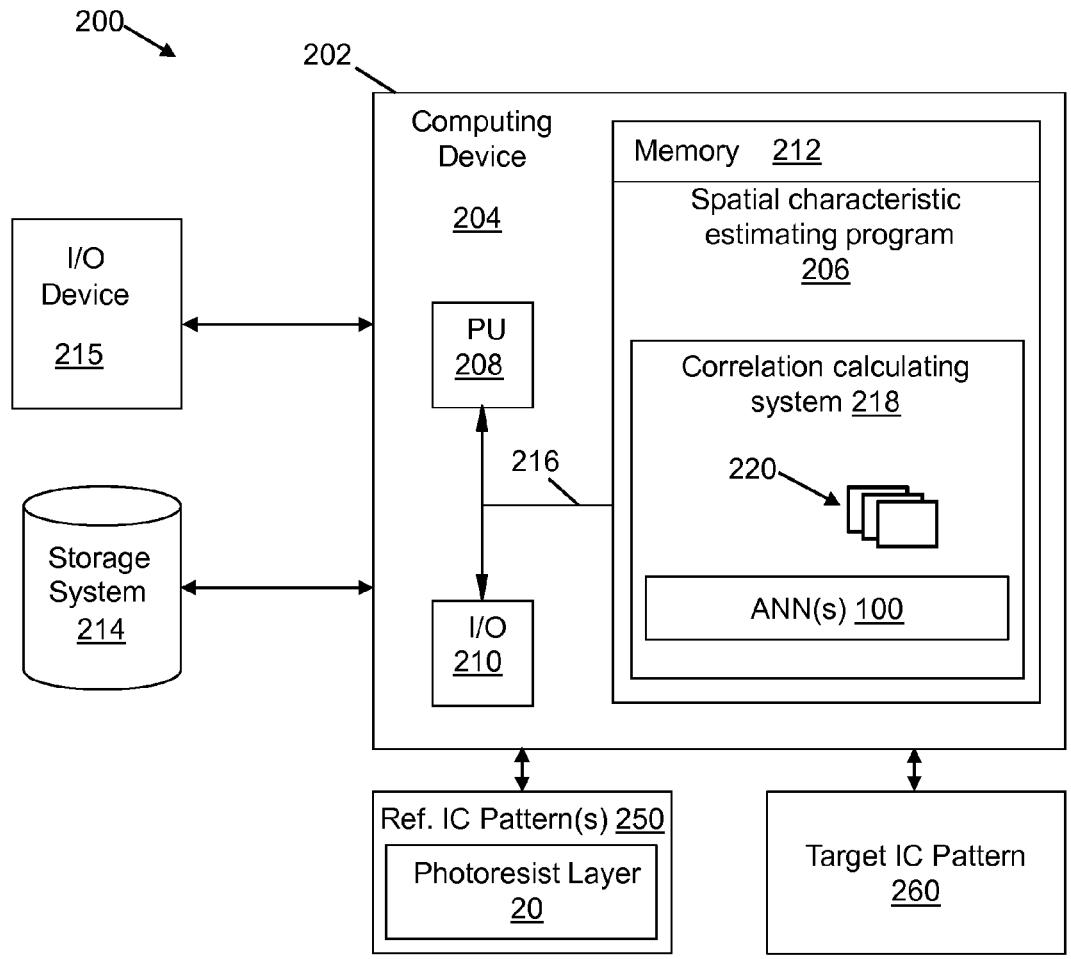
FIG. 4 depicts an illustrative environment which includes a computer system interacting with IC patterns according to an embodiment of the present disclosure.

Turning now to FIG. 4, an illustrative environment 200 for implementing the methods and/or systems described herein is shown. In particular, a computer system 202 is shown as including a computing device 204. Computing device 204 can include a spatial characteristic estimating program 206 which estimate spatial characteristics of ICs by performing any/all of the processes described herein and implementing any/all of the embodiments described herein.

Computer system 202 is shown including a processing unit 208 (e.g., one or more processors), an I/O component 210, a memory 212 (e.g., a storage hierarchy), an external storage system 214, an input/output (I/O) device 215 (e.g., one or more I/O interfaces and/or devices), and a communications pathway 216. In general, processing unit 208 can execute program code, such as spatial characteristic estimating program 206, which is at least partially fixed in memory 212. While executing program code, processing unit 208 can process data, which can result in reading and/or writing transformed data from/to memory 212 and/or I/O device 215 for further processing. Pathway 216 provides a communications link between each of the components in environment 200. I/O component 210 can comprise one or more human I/O devices, which enable a human user to interact with computer system 202 and/or one or more communications devices to enable a system user to communicate with the computer system 202 using any type of communications link. To this extent, spatial characteristic estimating program 206 can manage a set of interfaces (e.g., graphical user interface(s), application program interface(s), etc.) that enable system users to interact with spatial characteristic estimating program 206. Further, spatial characteristic estimating program 206 can manage (e.g., store, retrieve, create, manipulate, organize, present, etc.) data, through several modules contained within a correlation calculating system 218.

Further, spatial characteristic estimating program 206 can include a correlation calculating system 218. In this case, various modules of correlation calculating system 218 can enable computer system 202 to perform a set of tasks used by spatial characteristic estimating program 206, and can be separately developed and/or implemented apart from other portions of spatial characteristic estimating program 206. Correlation calculating system 218 can also include all or part of ANN 100, which can model and/or calculate a correlation between a particular dimension and SEM exposure as discussed herein.

Several modules 220 of correlation calculating system 218 can perform predetermined functions. For example, a determinator module of modules 220 can issue instructions, commands, etc. based on data stored within memory 212 of computing device 204, or other pieces of information provided thereto. A calculator module of modules 220 can perform mathematical computations. A comparator module of modules 220 can compare two or more calculated values and/or items of data as a preliminary step to determinations performed with other modules. Each module discussed herein can obtain and/or operate on data from exterior components, units, systems, etc., or from memory 212 of computing device 204. Correlation calculating system 218 of spatial characteristic estimating program 206 can model a correlation between exposure to an SEM (e.g., a top-down exposure) and one or more dimensions for at least one reference IC pattern 250. With this correlation, spatial characteristic estimating program 206 can estimate the spatial characteristics of a target IC pattern 260. Reference IC pattern(s) 250 can be converted into data and may be stored, e.g., within memory 212 of computing device 204, storage system 214, and/or any other type of data cache in communication with computing device 204. The features of reference IC pattern 250 (e.g., arrangements and/or features of photoresist layers 20) can be converted into data inputs or other inputs to spatial characteristic estimating program 206 with scanning devices and/or manual entry of a user.

Where computer system 202 comprises multiple computing devices, each computing device may have only a portion of spatial characteristic estimating program 206 and/or correlation calculating system 218 fixed thereon (e.g., one or more modules). However, it is understood that computer system 202 and spatial characteristic estimating program 206 are only representative of various possible equivalent computer systems that may perform a process described herein. Computer system 202 can obtain or provide data, such as data stored in memory 212 or storage system 214, using any solution. For example, computer system 202 can generate and/or be used to generate data from one or more data stores, receive data from another system, send data to another system, etc.

Figure 5:
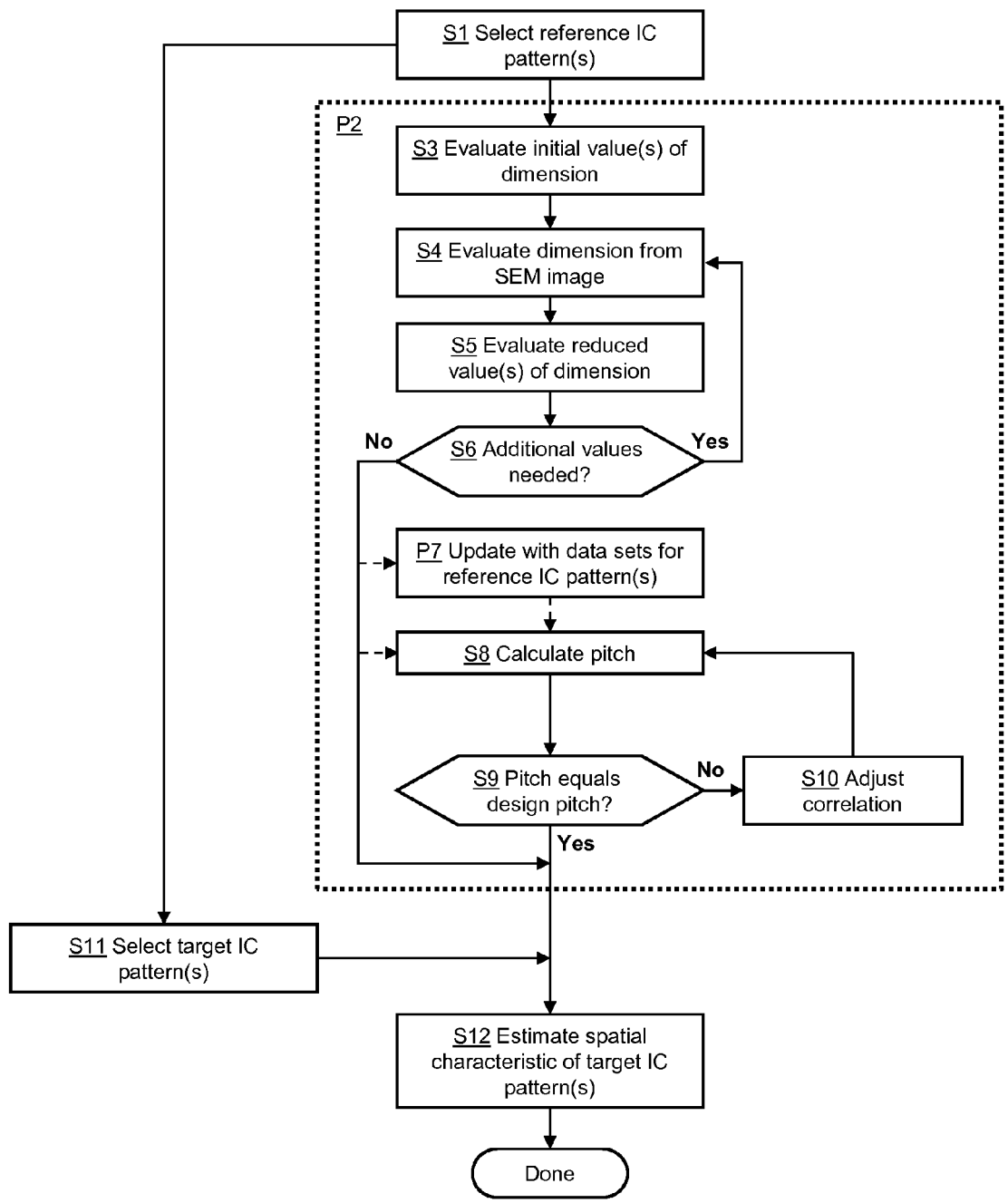
FIGS. 5-6 depict flow diagrams with illustrative method steps according to embodiments of the present disclosure.

Referring to FIG. 5 in conjunction with FIG. 4, a process flow diagram of methods according to the present disclosure is shown. The process flow diagram of FIG. 5 provides an overview of various method steps and processes, some of which are shown in greater detail in other FIGURES and described elsewhere herein. The steps and processes can each be carried out with the components shown in FIG. 4 and described herein by example. Embodiments of the present disclosure, as illustrated by example in FIG. 5, can calculate a correlation (e.g., by computing a model and/or training ANN 100) based on at least one reference IC pattern 250. Using the calculated correlation and one or more inputs (e.g., known dimensions and/or other spatial characteristics) of target IC 260 pattern, a machine user can estimate a spatial characteristic of target IC pattern 260.

To calculate the correlation as provided in embodiments, at least one reference IC pattern 250 is chosen in step S1 for determining the relationship between exposure to an SEM and one or more dimensions of a particular feature (e.g., photoresist layer 20). In step S1, a selecting module 220 of spatial characteristic estimating program 206 can select reference IC pattern 250 from one of several candidate patterns, e.g., by following predetermined software instructions for selecting one or more reference IC patterns 250 based on particular characteristics. Reference IC pattern 250 can include a particular photoresist layer 20 with spatial characteristics to be estimated. The selected reference IC pattern 250 can include the same pattern of features or a different pattern of features as the target IC pattern 260. Reference IC pattern 250 can include features which have not been reduced in size, e.g., from exposure to an SEM or from one or more other process steps discussed herein. In a particular embodiment, a dimension of reference IC pattern 250 can include critical dimension 40 (FIG. 1) with a magnitude of less than approximately forty nanometers. In another embodiment, as discussed in further detail herein, the spatial characteristic of reference IC pattern 250 can include the contour of a shape or feature. The contour can be defined and represented mathematically by use of, e.g., a particular formula for two dimensions of space. In any case, process flows in the present disclosure can proceed to a process P2 for training (otherwise known as "calibrating" or "supervised learning") of a model, such as a model defined in ANN 100, to accurately estimate the spatial characteristics of one or more target IC patterns 260.

Process P2 includes several steps S3 through S10 for calculating a correlation between a particular dimension and exposure to an SEM based on reference pattern 250 selected in step S1. The steps S3 through S10 of process P2 are illustrated as being in a particular order in FIG. 5. However, it is understood that some steps of process P2 can be omitted where appropriate and/or performed in a different order from what is discussed by example herein. Embodiments of process P2, as a whole, can calculate a correlation between one or more dimensions of photoresist layers 20 (FIG. 2) of the reference pattern before and/or after one or more exposures to an SEM. The correlation calculated and output from process P2 can be a function or mathematical formula which relates one or more dimensions of photoresist layers 20 with SEM exposure expressed as, e.g., a number of electrons emitted, a total exposure time of reference IC pattern 250 to an SEM, etc.

Process P2 can calculate the correlation between a dimension of an IC pattern with exposure to an SEM. Embodiments of the present disclosure can calculate the correlation by training ANN 100 or otherwise generating a model. The steps of process P2 can be performed to calculate the correlation using only one reference IC pattern 250. If desired, process P2 can be adapted for calculating the correlation based multiple reference IC patterns 250. Where multiple reference IC patterns 250 are used, each of the various reference IC patterns 250 may include the same layout of features or different layouts of features. The correlation calculated in process P2 can incorporate values of one or more dimensions from each reference IC pattern 250. The determined features of each reference IC pattern 250 can be incorporated into a generated model and/or ANN 100, either using a complete sample of measurements or representative statistical values. In any case, process P2 and the other steps discussed herein can be adapted to operate on each reference IC pattern 250 simultaneously, or in succession by repeatedly performing embodiments of the process flow discussed herein.

In process P2 at step S3, a user and/or component of computer system 202 can evaluate an initial value of one or more dimensions of photoresist layer 20 (FIG. 1). In an illustrative embodiment, the evaluation of the at least one dimension of photoresist layer 20 can include directly measuring the dimension (e.g., a length or width) of photoresist layer 20 with AFM probe 10 (FIG. 1) or obtaining a predetermined measurement. As used herein, the "dimension" of a feature of reference IC pattern 250 and/or target IC pattern 260 can include, e.g., a length, a width, a height, a contour, concavity, and/or any other quantity for measuring a feature of an IC, such as an opening of photoresist layer 20. A dimension of photoresist layer 20 determined in step S1 can be designated as the initial or beginning value for reference IC pattern 250. The evaluated dimension step S1 can be stored in memory 212 and/or elsewhere (e.g., storage system 214) as an "initial value" for the dimension of photoresist layer 20.

In step S4, one or more dimensions of reference IC pattern 250 can be evaluated by reference to an SEM image and/or measurements derived therefrom. Following the determination (e.g., by measurement) of an initial value for the dimension in step S3, a user, computer system 202, and/or unrelated party or system can scan reference IC pattern 250 with an SEM. As discussed elsewhere herein, exposing reference IC pattern 250 to an SEM can reduce the initial value determined in step S3 and/or the value of one or more dimensions of photoresist layer 20 (FIG. 1). This process also generates an SEM image of reference IC pattern 250 with measurements of the pattern. As is shown in FIG. 5 at steps S4 through S6 and discussed herein, step S4 can be repeated multiple times where reference IC pattern is exposed to multiple SEM scans. For each scan, the dimensions of reference IC pattern 250 may further decrease, and/or other changes to the features of reference IC pattern 250 may occur. A sequential exposure of reference IC pattern 250 thus can generate a trend in dimensional reduction. Applicants have discovered that this trend can very non-linearly for different reference IC patterns 250. To extract dimensional measurements, the image can be converted into a descriptive set of data with modules 220 of correlation calculating system 218 and/or a user thereof. The descriptive set of data for the SEM image(s) of reference IC pattern 250 can include, e.g., a set of dimensions for each element of reference IC pattern 250, including the width and/or length of photoresist materials in photoresist layer 20. The dimensions determined from the SEM image(s) in step S4 can be stored in memory 212 and/or elsewhere (e.g., storage system 214).

At step S5, a user and/or component of computer system 202 can determine a reduced value of one or more dimensions of photoresist layer 20 (FIG. 1). Determining the reduced dimension of photoresist layer 20 can include using AFM probe 10 (FIG. 1) to directly measure one or more of the dimensions determined in steps S3 and S4 and/or referring to a particular SEM image. The dimensions evaluated in step S3-S5, together, can indicate a rate of change for one or more dimensions of reference IC pattern 250 from exposure to an SEM. Depending on user requirements and/or the characteristics of reference IC pattern 250, several evaluations of a dimension may improve the accuracy of a generated mathematical relationship between the size of photoresist layer 20 and an amount of exposure to the SEM. In step S6, a determinator of modules 220 can determine whether a sufficient number of values for the dimension have been collected. This determination in step S6 can be based on, e.g., a comparator of modules 220 comparing between whether the number of SEM images and/or direct measurements has met or exceeded a particular threshold, instructions from user inputs (e.g., via I/O device 215), and/or other criteria. Where more data is needed (i.e., "Yes" at step S6), the flow can return to step S4 for determining the value of the dimension from one or more additional SEM images and/or direct measurements. Where additional SEM images are used to determine other values of the dimension, calculating the correlation in process P2 can be based on multiple SEM images for reference IC pattern 250, with the multiple SEM images further reducing the dimension(s) of photoresist layer 20. Where the number of measurements is sufficient (i.e., "No" at step S6), the flow can proceed to further steps for estimating spatial characteristics of an IC.

Figure 6:
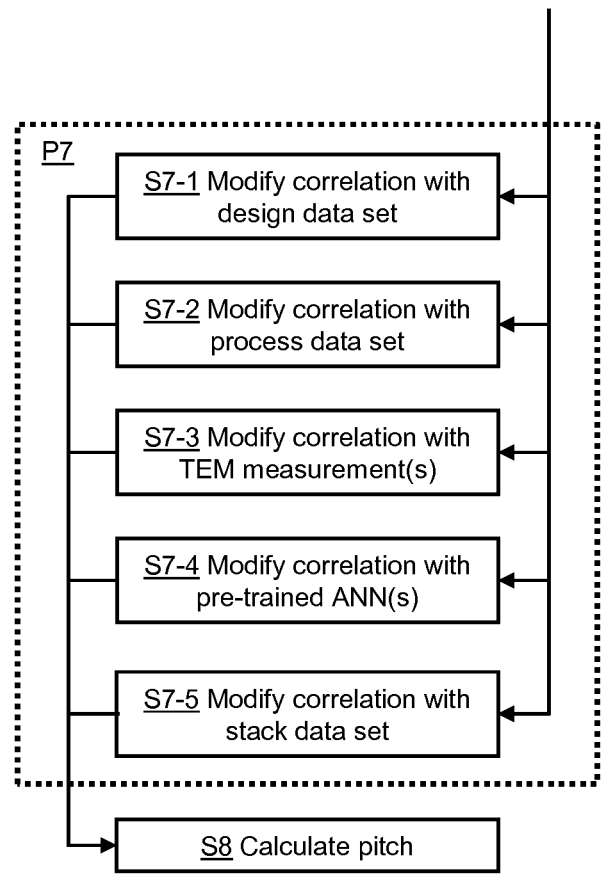

As illustrated by the corresponding phantom process flow line from step S6 to process P7 of FIG. 5, calculating the correlation between the dimension and exposure to an SEM in process P2 can incorporate additional variables. More specifically, process P2 can include sub-process P7 for factoring several types of data for the reference IC pattern 250 into the calculated correlation. Referring now to FIGS. 4 and 6 together, an example group of steps used in process P7 are shown. As is indicated in FIG. 6, sub-process P7 can be made up of several steps carried out together or separately.

In step S7-1, the correlation (which can affect the weights "W" of ANN 100) can be modified based on a design data set for reference IC pattern 250. The design data set can include a sample of reference data stored, e.g., in memory 212 and/or storage system 214, which can include designed and/or ideal characteristics of reference IC pattern 250. In an embodiment, the design data set can include one or more of the shape of a feature in a particular pattern (e.g., a shape in photoresist layer 20), one or more dimensions for particular features in the pattern, and/or a pitch (i.e., a sum of the width of a feature and the space on one side of the feature separating that feature from a neighboring feature) for reference IC pattern 250. The design data set can include other design features for reference IC pattern 250 not discussed explicitly herein. To incorporate the design data set into the correlation, the corresponding model can be updated to include adjusted variables, coefficients, constants, terms, etc. Where the correlation is calculated using ANN 100, the weights for nodes in hidden layer 106 (FIG. 3) can be adjusted to reflect corresponding data from the design data set. As an example, a predetermined design value of pitch for reference IC pattern 250 can define the distance between features of photoresist layer 20 of reference IC pattern 250, and thereby indicate a rate at which photoresist layer 20 decreases in size from exposure to an SEM.

In step S7-2, modules 220 can modify the correlation based on a process data set for the reference IC pattern 250. The process data set can generally include data relating to techniques for processing the reference IC pattern and/or elements thereon. The process data set can be stored, e.g., in memory 212 and/or storage system 214. A process data according to the present disclosure can include one or more of the following: a temperature at which features (e.g., photoresist layer 20 (FIG. 1)) are cured, a resolution enhancement technique applied to reference IC pattern 250 (e.g., a distortion correction, use of multiple patterning, applying a phase-shift mask and/or scattering bars, scanner dose and focus, and/or other techniques currently known or later developed), and/or forming and exposure conditions for reference IC pattern 250. The processing data set can also include other variables and/or adjustments related to other processing steps not discussed explicitly herein. To include the process data in the correlation modules 220 can adjust variables, coefficients, constants, terms, etc. of a generated model. In embodiments where the correlation is calculated via ANN 100, these adjustments can include changing the weights for nodes in hidden layer 106 to reflect corresponding data from the process data set. As an example, different processing temperatures may cause reference IC pattern 250 to decay faster or slower from exposure to an SEM than other IC patterns which are processed at different temperatures during particular fabrication steps.

In step S7-3, modules 220 can also modify the correlation based on other measurements of reference IC pattern 250 performed with a transmitting electron microscope (TEM). More specifically, the correlation can be based in part on reference IC pattern 250 after etching or other process steps transfer a pattern for photoresist layer 20 (FIG. 1) into a particular dielectric layer. The post-etch TEM measurements can illustrate further spatial characteristics related to the dimension measured in steps S3 through S5 of process P2 discussed elsewhere herein. The TEM measurements can be stored, e.g., in memory 212 and/or storage system 214. As with other types of data, modules 220 can mathematically adjust one or more variables, coefficients, constants, terms, etc. of a model to change the correlation based on TEM measurements. In embodiments where the correlation is calculated via ANN 100, the weights for nodes in hidden layer 106 (FIG. 3) can be increased or decreased based on data from the TEM measurements. As an example, post-etch TEM measurements can provide more data points for a particular dimension (e.g., data points on a trend line) for calculating the effect of SEM exposure on a dimension of a feature of reference IC pattern 250.

In step S7-4, modules 220 of computer system 202 can modify the correlation based on the weights of an artificial neural network. In one example, where correlation calculating system 218 includes ANN 100, the weights for various nodes within hidden layer 106 (FIG. 1) can be increased, decreased, etc. based on the weights for another ANN 100 in communication with computer system 202. One or more other ANNs 100 may have previously modeled an IC pattern, and in some circumstances may be "pre-trained." A "pre-trained" ANN refers to an ANN with weights which were previously adjusted by reference to other related or unrelated sets of data, and which may not be subject to further adjustments. Computer system 202 may be capable of reading and/or copying data from other ANNs 100 by, e.g., including multiple ANNs 100 in memory 212 and/or being coupled to other computer systems by any currently known or later developed networking hardware and/or software, optionally through I/O device 215. Incorporating other ANN models into the correlation can also include directly adjusting a non-ANN model based on data from a particular ANN, regardless of whether ANN 100 calculates the correlation in process P2 (FIG. 5). In any case, modules 220 can read data from a particular ANN and perform operations to adjust one or more variables, coefficients, constants, terms, etc., of a model and/or weights of ANN 100 to adjust the correlation. As an example, correlations calculated from other reference IC patterns 250 may reflect user-defined or previously discovered factors defined by, e.g., training ANN 100 by reference to different sets of ideal values.

In step S7-5, modules 220 can modify the correlation based on a stack data set for reference IC pattern 250. The stack data set can include characteristics of reference IC pattern 250 not included in the same layer as is measured in steps S3 through S5. For example, the stack data set can include a thickness and/or material composition of an IC layer adjacent to the examined layer of reference IC pattern 250. The stack data set can also include a thickness and/or material composition of the layer where reference IC pattern 250 is located, another layer of a different IC having the same design or a different design, etc. The stack data set of step S7-5 set can be stored, e.g., in memory 212 and/or storage system 214. The stack data set can also include other characteristics of a particular IC not discussed explicitly herein. Modules 220 of correlation calculating system 218 can adjust variables, coefficients, constants, terms, etc. to enhance the model for calculating the coefficient in step S7-5. In embodiments where the correlation is calculated via ANN 100 (FIG. 3), modules 220 can adjust the weights for nodes in hidden layer 106 to reflect corresponding data from the stack data set. As an example, SEM degradation of reference IC pattern 250 can increase or decrease based on the material composition of substrate 30 (FIG. 1) or other adjacent materials. In step S7-6, modules 220 can modify the correlation based on electrical test data (such as measured values of resistance and/or capacitance) set for reference IC pattern 250. The electrical tests can be performed after metal is filled in the space patterns of reference IC pattern 250 and polished. The electrical performance of reference IC pattern 250 can be related to, e.g., the dimensions and profiles within reference IC pattern 250.

Returning to FIGS. 4 and 5, further steps of a process flow for estimating a spatial characteristic of an IC are discussed. As is shown by the corresponding phantom process flow lines from sub-process P7 and step S6 to step S8, embodiments of the method can optionally include calculating a pitch of reference IC pattern 250 using a preliminary value of the correlation yielded from steps S3 through S5. The adjustments from sub-process P7 can also be included in the correlation to calculate values of pitch. In process steps S8 through S10, the pitch serves as a reference variable for determining whether the calculated correlation is accurate for known measurements of reference IC pattern 250 and/or target IC pattern 260. As discussed elsewhere herein, the pitch specifies a sum of the width of a feature (e.g., a portion of photoresist layer 20 (FIG. 1) and the space on one side of the feature separating that feature from a neighboring feature (e.g., another portion of photoresist layer 20 or another feature of reference IC pattern 250). To calculate the pitch in step S8, the correlation from a single ANN 100 can calculate the pitch for reference IC pattern 250 based on initial values of one or more dimensions. In an alternative embodiment, modules 220 of correlation calculating system 218 can calculate the correlation using two or more ANNs 100, with one ANN 100 for modeling dimensions of lines of photoresist layer 20, and another ANN 100 for modeling dimensions of trenches in reference IC pattern 250. A single ANN 100 can alternatively include nodes for modeling dimensions of both lines and trenches in reference IC pattern 250.

In step S9, a determinator module 220 of correlation calculating system 218 can determine whether the calculated pitch of step S8 is "equal" to a predetermined design pitch, which can also be known as a reference pitch or an ideal pitch. In this context, it is understood that the term "equal" may include situations other than two compared variables being of equal value. For example, being "equal" may include the calculated pitch being within a particular margin of error for one design pitch and/or may be equal to one of several design pitches. In any case, the determination in step S9 can be based on a comparator of modules 220 comparing the calculated pitch against the design pitch (whether in the form of a single value, group of values, or range). The design pitch may be stored, e.g., in memory 212 and/or storage system 214. In addition or alternatively, the design pitch can be part of a design data set for adjusting the correlation in sub-process S7 as discussed elsewhere herein. Where the calculated pitch "equals" the design pitch (i.e., "Yes" at step S9), the flow can proceed to other steps for estimating spatial characteristic of an IC described elsewhere herein. Where the calculated pitch of step S8 does not "equal" the design pitch (i.e., "No" at step S9), the flow can proceed to a step S10 for adjusting the correlation, e.g., by adjusting variables, coefficients, constants, terms, etc. of a model and/or adjusting the weight of nodes in hidden layer 106 (FIG. 1) of ANN 100 (FIG. 1). Following the adjustment of step S10, the flow can return to step S8 where modules 220 of correlation calculating system 306 can recalculate the pitch and determine again in step S9 whether the calculated pitch "equals" the design pitch.

Following the calculating of the correlation in process P2, and optional verifying with the design pitch, the produced correlation can be used to estimate one or more spatial characteristics of target IC pattern 260. The correlation can be in the form of, e.g., a data trend and/or associated function which relates a particular dimension (e.g., a length, width, height, etc. of a feature such as a photoresist material of photoresist layer 20) with exposure to an SEM, whether in terms of time, terms of total electron exposure, and/or other metrics. In step S11, which may occur in parallel with calculating the correlation in process P2, components of computer system 202 and/or a user thereof can select target IC pattern 260 with spatial characteristics to be estimated according to embodiments of the present disclosure. The target IC pattern(s) 260 can be different from reference IC pattern 250 or can be the same IC pattern after being exposed to one or more SEM scans. Target IC pattern 260 can include, e.g., one or more features with an unknown contour and/or critical dimensions with a magnitude of less than approximately 40 nm, and thus may not be measurable with a physical probe (e.g., AFM probe 10 (FIG. 1)).

In step S12, an input for the target IC pattern(s) 260 of step S11 can be provided to the model and/or ANN 100 with the calculated correlation from process P2. In an example embodiment, AFM probe 10 (FIG. 1) can measure one feature of target IC pattern 260 which is large enough for direct measurement (e.g., includes a dimension larger than forty nm). This measurement can be an input to estimate dimensions of other features in target IC pattern 260 which are not measurable with a physical probe. In another example embodiment, several features of target IC pattern 260 can be measured with AFM probe 10 before the IC pattern is scanned with an SEM, causing several dimensions to be reduced below the minimum size detectable with a physical probe. The initial measurements of target IC pattern 260 can be used with the correlation as inputs to calculate a dimension of a feature of target IC pattern 260 after the SEM scan.

Using a particular model or an ANN 100 adjusted with the data and/or outputs of process P2, one or more spatial characteristics of target IC pattern 260 can be estimated using spatial characteristic estimating program 206 in step S12. In an embodiment, the estimated spatial characteristic(s) of target IC pattern 260 can include the magnitude of critical dimension 40 (FIG. 1). In another embodiment, the estimated spatial characteristic can include a contour or geometry of a feature of target IC pattern 260. Following this estimation, the method can conclude. In addition or alternatively, the method can repeat for target IC pattern 260 or a different IC pattern, and the correlation calculated in process P2 can be determined again and/or updated with information estimated for or measured from target IC pattern 260 and/or other reference IC patterns 250. Thus, technical effects of the present disclosure can include estimating one or more spatial characteristics of one or more ICs.

Figure 7:
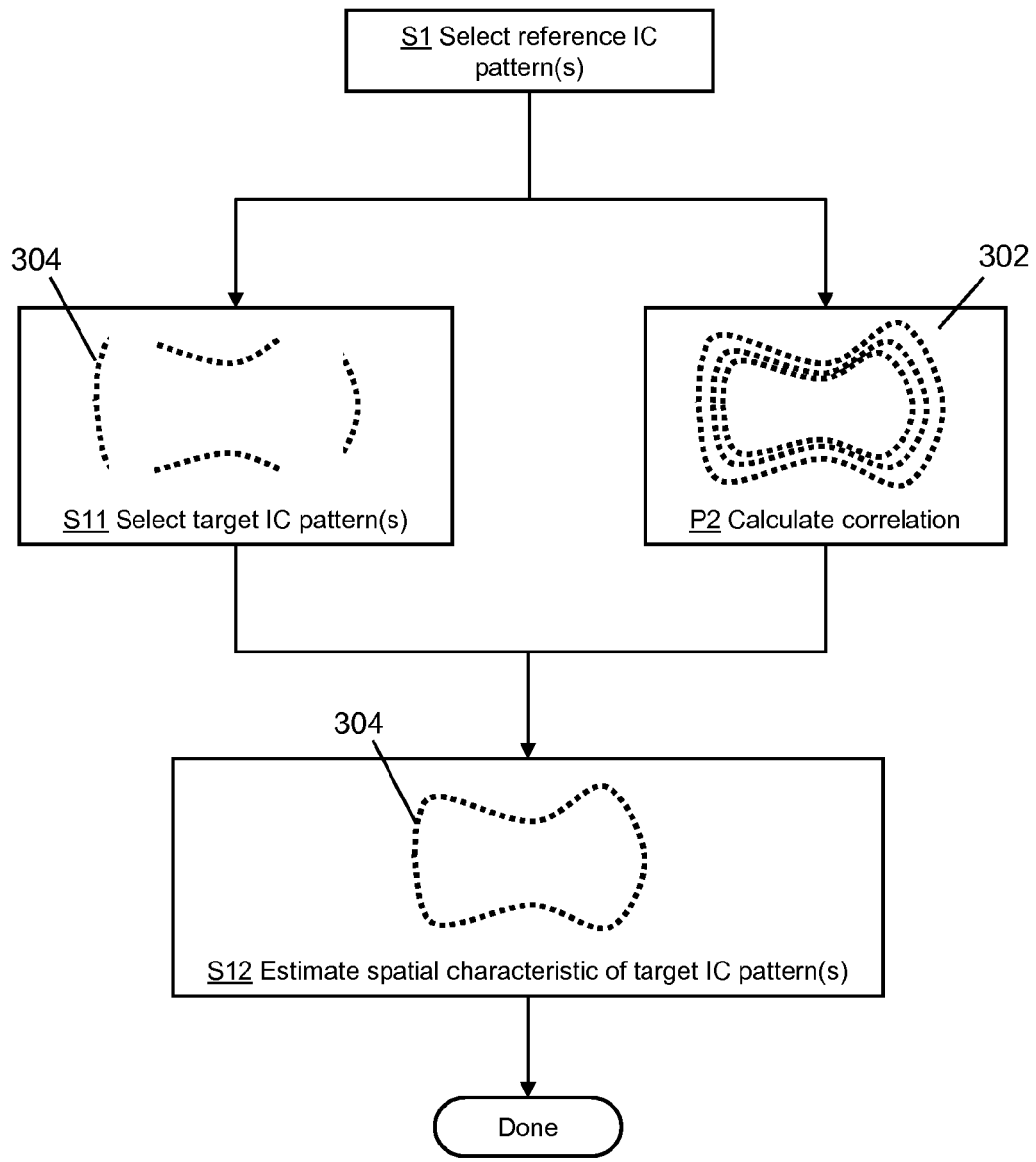
FIG. 7 depicts a schematic flow diagram with illustrative method steps according to embodiments of the present disclosure.

Turning to FIG. 7, a schematic flow diagram of an embodiment of the present disclosure for determining a shape contour of target IC pattern 260 is shown. As is illustrated in FIG. 7, the same steps discussed above with reference to FIGS. 4-6 can be adapted to measure and estimate the contour of one or more shapes as a "spatial characteristic" of target IC pattern 260. In general, shapes or other features of photoresist layer 20 can be in a substantially rectangular shape. However, it is understood that embodiments of the present disclosure can estimate the contour of any desired shape. For the purposes of illustration, the shapes depicted in FIG. 7 by example include at least partially rectangular shapes.

In step S1, a user and/or modules of 220 of correlation calculating system 218 can select reference IC pattern(s) 250 for calculating a correlation between one or more dimensions and exposure to an SEM. Step S1 can also include measuring, extracting, or otherwise obtaining a reference contour from the selected reference IC pattern(s) (e.g., using an AFM probe). In process P2, direct measurements (e.g., measurements with AFM probe 10 (FIG. 1)) and one or more SEM measurements can be collected for reference IC pattern 250, including reference contours from step S1, to determine the correlation. In some embodiments, process P2 can include performing multiple SEM measurements, with each measurement reducing the size of the reference IC pattern. As is shown in FIG. 7, a reference contour 302 can reduce in size, or "shrink" after exposure to the SEM. As is discussed herein, the calculating of the correlation in process P2 can mathematically train one or more ANNs 100 (FIG. 4) to generate a relationship between SEM exposure and particular spatial characteristics. ANNs 100, in an embodiment, can be trained using the decreasing contours for reference contour 302.

In step S11, a user and/or component of computer system 202 can select a particular target IC pattern 260 with a target shape contour 304. Target shape contour 304 may be partially measured, e.g., directly with AFM-probe 10 (FIG. 1), but may include regions or features incapable of being measured with the physical probe, as is indicated in FIG. 7. To accurately estimate the remaining regions or features of target shape contour 304, the correlation and the measured features of target shape contour 304 can be used as inputs into a generated model and/or ANN in step S12 to estimate a spatial characteristic (e.g., dimensions, sidewall angles, roughness, contours, complete profile, etc.) of target shape contour 304, without an SEM measurement of target IC pattern 260 being required. In an embodiment, ANN(s) 100 (FIG. 4) can estimate this spatial characteristic using the calculated correlation from process P2, the target IC pattern(s) from step S11, and generating a model using a multidimensional mathematical process carried out in design space.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present invention may take the form of a computer program product embodied in one or more computer readable medium(s) having computer readable program code embodied thereon.

Any combination of one or more computer readable medium(s) may be used. A computer readable storage medium may be, for example, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As used herein, the term "configured," "configured to" and/or "configured for" can refer to specific-purpose features of the component so described. For example, a system or device configured to perform a function can include a computer system or computing device programmed or otherwise modified to perform that specific function. In other cases, program code stored on a computer-readable medium (e.g., storage medium), can be configured to cause at least one computing device to perform functions when that program code is executed on that computing device. In these cases, the arrangement of the program code triggers specific functions in the computing device upon execution. In other examples, a device configured to interact with and/or act upon other components can be specifically shaped and/or designed to effectively interact with and/or act upon those components. In some such circumstances, the device is configured to interact with another component because at least a portion of its shape complements at least a portion of the shape of that other component. In some circumstances, at least a portion of the device is sized to interact with at least a portion of that other component. The physical relationship (e.g., complementary, size-coincident, etc.) between the device and the other component can aid in performing a function, for example, displacement of one or more of the device or other component, engagement of one or more of the device or other component, etc.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for estimating a spatial characteristic of an integrated circuit (IC), the method comprising:
   calculating a correlation between a dimension of a photoresist layer and exposure to a scanning electron microscope (SEM) for at least one reference IC pattern in the photoresist layer, the correlation providing a relationship between the dimension of the photoresist and the spatial characteristic, wherein the calculating is based on:
      at least one measurement derived from an SEM image of the at least one reference IC pattern produced from reducing the dimension of the photoresist layer with the SEM from an initial value to a reduced value,
      the initial value of the dimension, and
      the reduced value of the dimension; and
   estimating the spatial characteristic of a target IC based on the correlation.

2. The method of claim 1, wherein the calculating of the correlation further comprises training a model of the correlation in an Artificial Neural Network (ANN) using the at least one measurement derived from the SEM image, the initial value of the dimension, and the reduce value of the dimension.

3. The method of claim 1, wherein one of the initial value and the reduced value of the dimension is measured with an atomic force microscopy (AFM) probe.

4. The method of claim 1, wherein the calculating of the correlation is further based on a design data set including one of a shape, a dimension, and a pitch for the at least one reference IC pattern.

5. The method of claim 1, wherein the calculating of the correlation is further based on a process data set including one of a curing temperature, a resolution enhancement technique, and an exposure condition for the at least one reference IC pattern.

6. The method of claim 1, wherein the calculating of the correlation is further based on a transmitting electron microscope (TEM) measurement of the at least one reference IC pattern following an etch of the photoresist layer.

7. The method of claim 1, wherein the calculating of the correlation is further based on a stack data set including a layer thickness and a material composition of at least one layer of the at least one reference IC pattern.

8. The method of claim 1, wherein the calculating of the correlation is further based on electrical test data from at least one other IC pattern.

9. The method of claim 1, wherein the calculating of the correlation is further based on a plurality of SEM images of the at least one reference IC pattern, each of the plurality of SEM images having reduced the dimension of the photoresist layer.

10. The method of claim 1, wherein the spatial characteristic of the target IC pattern comprises one of a critical dimension having a magnitude of less than approximately 40 nanometers (nm) and a shape contour.

11. A non-transitory computer readable storage medium, the program product operative to estimate a spatial characteristic of an integrated circuit (IC) when executed, the computer readable storage medium comprising program code for:
calculating, using an artificial neural network (ANN), a correlation between a dimension of a photoresist layer and exposure to a scanning electron microscope (SEM) for at least one reference IC pattern including the photoresist layer, the correlation providing a relationship between the dimension of the photoresist and the spatial characteristic, wherein the calculating is based on:
at least one measurement derived from an SEM image of the at least one reference IC pattern produced from reducing the dimension of the photoresist layer with the SEM from an initial value to a reduced value,
the initial value of the dimension, and
the reduced value of the dimension; and
estimating the spatial characteristic of a target IC based on the correlation.

12. The non-transitory computer readable storage medium of claim 11, wherein the calculating of the correlation is further based on a pre-trained ANN model of at least one other IC pattern.

13. The non-transitory computer readable storage medium of claim 11, further comprising program code for:
calculating a pitch of the at least one reference IC pattern from the correlation after the at least one reference IC pattern is scanned with the SEM; and
in response to the calculated pitch not being equal to a design pitch, adjusting the correlation based on the design pitch.

14. The non-transitory computer readable storage medium of claim 11, wherein the calculating of the correlation is further based on a design data set including one of a shape, a dimension, and a pitch for the at least one reference IC pattern.

15. The non-transitory computer readable storage medium of claim 11, wherein the calculating of the correlation is further based on a process data set including one of a curing temperature, a resolution enhancement technique, and an exposure condition for the at least one reference IC pattern.

16. The non-transitory computer readable storage medium of claim 11, wherein the calculating of the correlation is further based on a post-etch transmitting electron microscope (TEM) measurement of the at least one reference IC pattern.

17. The non-transitory computer readable storage medium of claim 11, wherein the calculating of the correlation is further based on a stack data set including a layer thickness and a material composition of at least one layer of the at least one reference IC pattern.

18. The non-transitory computer readable storage medium of claim 11, wherein the at least one reference IC pattern comprises a plurality of reference IC patterns, and calculating of the correlation is further based on:
an initial dimension of a photoresist layer for each of the plurality of reference IC patterns;
at least one measurement derived from a respective SEM image for each of the plurality of reference IC patterns produced from using an SEM to reduce the dimension of the photoresist layer from the initial dimension to a reduced dimension, and
the reduced dimension of the photoresist layer for each of the plurality of reference IC patterns.

19. The non-transitory computer readable storage medium of claim 11, wherein estimating the spatial characteristic of the target IC pattern includes calculating one of a critical dimension having a magnitude of less than approximately 40 nanometers (nm) and a shape contour.

20. A system for estimating a spatial characteristic of an Integrated Circuit (IC), the system comprising:
a computing device in communication with a scanning electron microscope (SEM) and an atomic force microscopy (AFM) probe, and including program code for:
calculating a correlation between a dimension of a photoresist layer and exposure to the scanning electron microscope (SEM) for at least one reference IC pattern including the photoresist layer, the correlation providing a relationship between the dimension of the photoresist and the spatial characteristic, wherein the calculating is based on:
at least one measurement derived from an SEM image of the at least one reference IC pattern produced from reducing the dimension of the photoresist layer with the SEM from an initial value to a reduced value,
the initial value of the dimension, and
the reduced value of the dimension, wherein one of the initial value and the reduced value of the dimension are obtained with the AFM probe; and
estimating the spatial characteristic of a target IC based on the correlation.

* * * * *